United States Patent [19]

Lepie

[11] Patent Number: 5,119,941
[45] Date of Patent: Jun. 9, 1992

[54] MATCHBOOK-LIKE PERSONAL DENTAL AND NAIL HYGIENE APPARATUS AND METHOD

[76] Inventor: Eric J. Lepie, 2717 N. Magnolia, Tucson, Ariz. 85712

[21] Appl. No.: 617,150

[22] Filed: Nov. 23, 1990

[51] Int. Cl.⁵ .................. A24F 27/00; B65D 73/00
[52] U.S. Cl. ................................. 206/102; 206/38; 206/63.5; 206/473; 206/474; 206/581; 206/104
[58] Field of Search ............... 206/96, 102, 103, 104, 206/108, 38, 63.5, 581, 472, 473, 474, 475; 132/309, 323

[56] References Cited

U.S. PATENT DOCUMENTS

| | | | |
|---|---|---|---|
| D. 138,698 | 9/1944 | Salfisberg | 206/472 X |
| D. 211,880 | 8/1968 | Di Giuseppe | D24/1 |
| D. 250,132 | 10/1978 | Axelson | D28/64 |
| D. 257,912 | 1/1981 | Kuen-Yi | D3/30 |
| D. 309,959 | 8/1990 | Endelson et al. | D28/64 |
| 1,382,459 | 6/1921 | Bercovici | 206/102 X |
| 1,503,063 | 7/1924 | Perry | 206/63.5 |
| 1,598,101 | 8/1926 | Newman | 206/472 X |
| 1,672,766 | 7/1926 | March | 206/96 X |
| 1,832,604 | 11/1931 | Wupper | |
| 1,895,233 | 1/1931 | Rossen | 206/457 |
| 2,109,318 | 2/1938 | Lichter | 206/64 |
| 2,118,634 | 5/1938 | Williams | 206/104 |
| 2,268,379 | 12/1941 | Bird et al. | 206/103 |
| 2,269,196 | 1/1942 | Fried | 206/103 |
| 2,271,155 | 1/1942 | Rapaport et al. | 206/103 |
| 2,303,986 | 12/1942 | Carvos | 132/73 |
| 2,319,560 | 5/1943 | Salfisberg | 206/474 |
| 2,336,234 | 12/1943 | Evans | 206/29 |
| 2,547,779 | 4/1951 | Renyck | 206/472 |
| 2,771,886 | 11/1936 | Miller et al. | 206/102 X |
| 2,783,877 | 3/1957 | Volckening et al. | 206/474 |
| 3,438,486 | 4/1969 | Pinkas | 206/56 |
| 3,871,517 | 3/1975 | Cioffi | 206/108 |
| 3,902,509 | 9/1975 | Tundermann et al. | 132/84 |
| 3,970,193 | 7/1976 | Christensen | 206/104 |
| 4,328,892 | 5/1982 | Heitlinger | 206/229 |
| 4,471,874 | 9/1984 | Morane | 206/581 |
| 4,807,752 | 2/1989 | Chodorow | 206/63.5 |
| 4,828,108 | 5/1989 | Roth et al. | 206/63.5 X |
| 4,917,236 | 4/1990 | Galvez-Moran | 206/96 X |
| 4,934,523 | 6/1990 | Strom | 206/63.5 |

FOREIGN PATENT DOCUMENTS

| | | | |
|---|---|---|---|
| 0584700 | 10/1959 | Canada | 206/474 |
| 2106778 | 8/1971 | Fed. Rep. of Germany | 206/103 |
| 0063042 | 7/1955 | France | 206/103 |
| 0202685 | 4/1939 | Switzerland | 206/102 |
| 0004124 | of 1906 | United Kingdom | 206/102 |

OTHER PUBLICATIONS

Popular Mechanics Magazine, Nov. 1937 p. 38A.

Primary Examiner—Paul T. Sewell
Assistant Examiner—Ted Kavanaugh
Attorney, Agent, or Firm—Victor Flores

[57] ABSTRACT

A personal hygiene apparatus in matchbook form including a folded matchbook-like structure, that includes a plurality of individually packaged dental floss members detachably secured to the matchbook-like structure and toothpick accessory formed from the flap portion of the matchbook-like structure and at least one abrasive strip detachably secured to the flap closure receiving end of the matchbook-like structure for manicuring a user's nails. The apparatus also includes, in addition to the dental and nail hygiene accessories, a breath freshening mint and matches as other personal accessories.

4 Claims, 3 Drawing Sheets

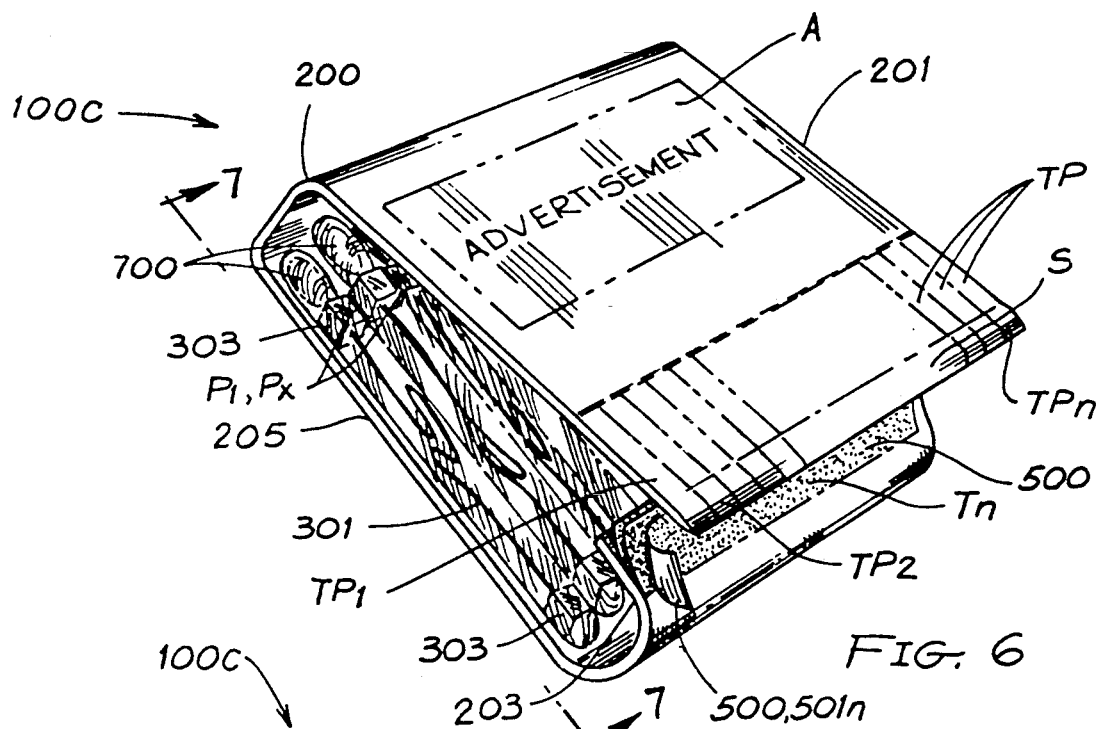
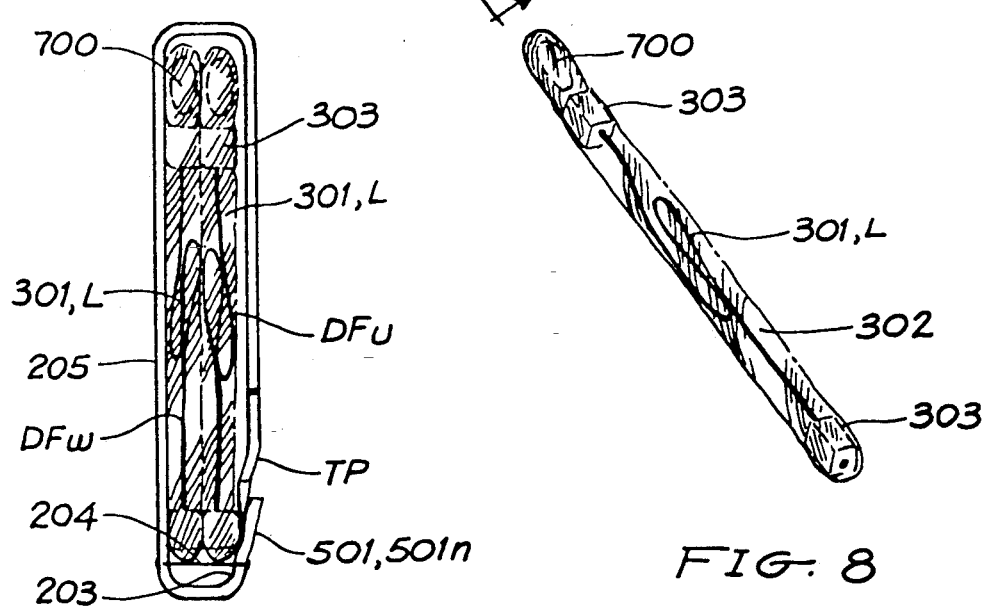
FIG. 6
FIG. 7
FIG. 8

MATCHBOOK-LIKE PERSONAL DENTAL AND NAIL HYGIENE APPARATUS AND METHOD

FIELD OF THE INVENTION

This invention relates to personal hygiene accessories. More particularly, the present invention relates to personal hygiene accessories relating to the dental and nail care. Even more particularly, the present invention relates to dental and nail hygiene accessories packaged in a matchbook-like structure that includes the dental and nail care accessories or may include the dental and nail hygiene accessories, complementing an array of matches.

DESCRIPTION OF THE PRIOR ART

The closest prior art relating to the present invention includes patented devices that have used the matchbook folded structure for supporting a variety of accessories for personal use that are in compact form and easy to carry. These patents include U.S. Pat. Nos. 1,832,604; 2,303,986; 2,336,234; 3,438,486 and 3,902,509. U.S. Pat. No. 1,832,604 to Wupper teaches a package containing any number of rows and files of rubber strands used as rubber dental cleaners. The patent is of interest for its teaching of individual, removable dental cleaners, the manner of packaging, namely the folded cardboard structure and the teaching away of the use of thread-like material, presumably dental floss. U.S. Pat. Nos. 2,336,234 and 3,438,486 are of interest for teaching the use of a matchbook structure to support various personal care and other personal utility devices. The '234 patent teaches including matches along with a plurality of toothpicks. The foregoing patents do not, however, teach the use of personal care devices supported by the matchbook structure in combination with personal care items that are integral with the matchbook structure.

One personal care item, namely the toothpick, traditionally thought of as an elongated circular apparatus having pointed ends, lends itself well for packaging within a matchbook-like structure. It is also well known that humans will occasionally use any available small pointed object to remove food particles from between the teeth. One commonly used object is the corner of the matchbook flap. One drawback from using the corner of the matchbook flap is that moisture softens the pointed corner, typically before the food removal task is complete. Other forms of toothpicks taught by U.S. Pat. No. 3,902,509 to Tundermann et al. include a disposable device for cleaning teeth in the form of finger pockets assembled and packaged in matchbook type folders. The Patent is of interest for its teaching of using the lap edges of moisture proof, dental cleaning finger pockets, as toothpicks. This prior art also fails to capitalize on the matchbook structure for providing a personal care item integral with the supporting matchbook-like stucture.

Another personal care item that lends itself well for capitalizing on the matchbook structure is the emery board accessory for nail care. U.S. Pat. No. 2,303,986 to Carvos teaches a manicure packet containing an assortment of nail manicure devices includes removable strips carrying abrasive material. The patent is of interest for its package style and matchbook-like stucture and the manner of providing the abrasive strips that are not integral to the matchbook structure.

Patents teaching state of the art in dental cleaner and dental floss dispensers include U.S. Pat. Nos. 4,934,523; 4,807,725; U.S. Pat. No. Des 309,959; U.S. Pat. No. Des. 257,912; U.S. Pat. No. Des. 250,132 and U.S. Pat. No. Des 211,880.

U.S. Pat. No. 2,109,318 to Lichter teaches a mending kit packaged in a matchbook-like structure.

Thus, while the prior art has taught the use of the matchbook structure for detachably supporting a variety of personal care accessories, the prior art has failed to adapt the matchbook structure to provide personal care accessories, such as toothpick and nail care accessories that can be made integral with the matchbook structure.

Therefore, a need is seen to exist for a personal care/hygiene apparatus in a matchbook-like stucture that not only includes detachable accessories but also includes personal care accessories that are integral with the matchbook-like structure.

More particularly, a need is seen to exist for a personal care apparatus in a matchbook-like structure that includes detachable individual dental floss accessories and also includes conditioned integral corners of the closure flap member of the matchbook-like structure for occasional use as personal toothpick object.

Even more particularly a need is seen to exist for a personal care apparatus in a matchbook-like structure that includes detachable individual dental floss accessories along with a breath freshening substance, conditioned integral corners of the closure flap member of the matchbook-like structure for occasional use as personal toothpick object and further includes providing the integral strike portion of a matchbook-like structure with integral layers of emery board items for use in manicuring a user's nails.

A need is further seen the exist for a matchbook apparatus that primarily contains matches yet, also includes the above personal care accessories, such as dental floss and those integral matchbook portions conditioned for being used as personal care item such as toothpicks and nail emery boards.

SUMMARY OF THE INVENTION

Accordingly, the primary object of the present invention is to provide a personal hygiene apparatus in matchbook form including a folded matchbook-like structure, a plurality of individually packaged dental floss members detachably secured to said structure, pointed means integral with said matchbook-like structure for removing food particles from a user's teeth and at least one abrasive material means detachably secured to said structure for manicuring a user's nails.

The foregoing object is accomplished by providing a personal hygiene apparatus having said plurality of individually packaged dental floss members comprising a strand of dental floss having a predetermined length and an enclosure for enclosing the individual dental floss strand and, in one embodiment, also for enclosing a breath freshening mint. Each dental floss member being joined to an adjacent, similarly packaged dental floss member via perforated means between respective enclosures for easy tearing by a user. The integral toothpick accessory is provided by specially coating the corners of the flap closure member of the matchbook-like structure with a non-toxic, moisture resistant plastic material. The emery board items are provided as integral strips in what is the strike equivalent portion of the matchbook structure.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

BRIEF DESCRIPTION OF THE DRAWINGS

FIG. 6 is an alternative embodiment of the present invention showing the individual, detachable dental floss members having a grip member at each end, a breath freshening substance packaged adjacent one of the grip members and illustrating an alternative matchbook flap closure structure having break-away strips useable as toothpick items, and further showing layered strips of emery board items at a strike equivalent portion, each with a different surface texture.

FIG. 7 is an cross-sectional end view taken along line 7—7 in FIG. 6 illustrating the enclosed length of dental floss looped between the grip members and further showing the breath freshening substance packaged at one end adjacent one of the grip members.

FIG. 8 is a perspective view of an individual dental floss member after being separated from the packaged accessories shown in FIG. 6.

DESCRIPTION OF THE PREFERRED EMBODIMENT

Figure 1:
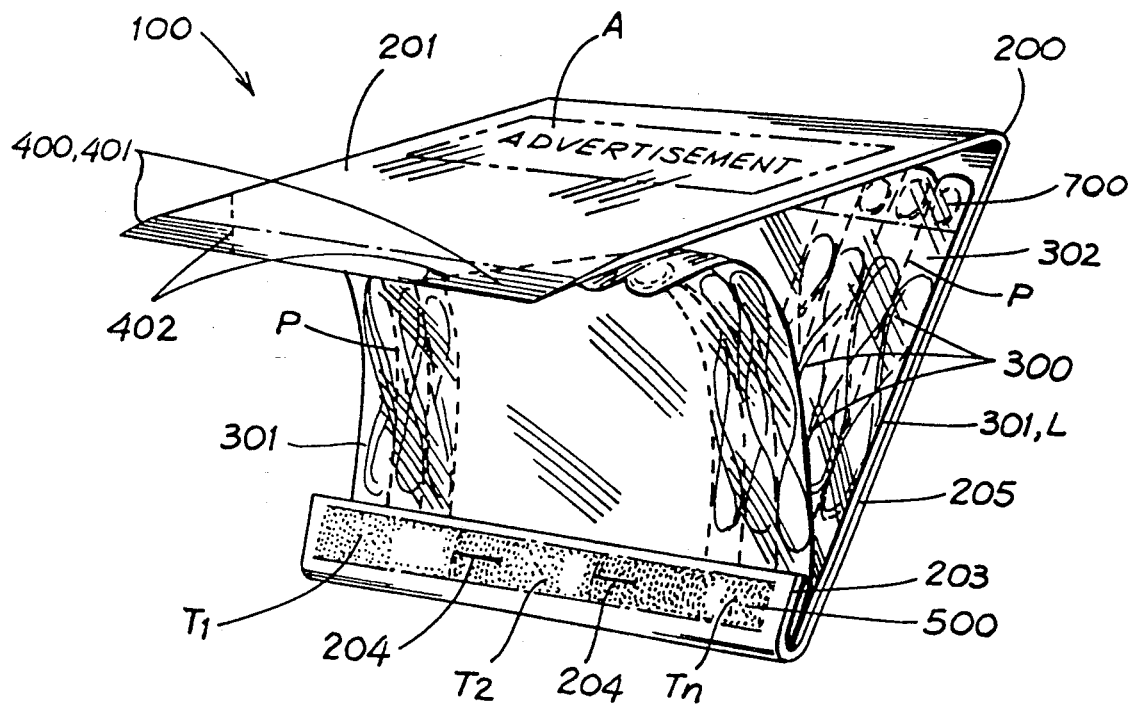
FIG. 1 is a perspective view of the present invention illustrating a matchbook-like structure with a plurality of detachable dental floss accessories and utilization of adapted portions of the matchbook-like structure for other personal care accessories.

FIG. 1 illustrates the preferred embodiment of the present invention where a personal hygiene apparatus 100 is provided in a matchbook-like structure 200 and personal care accessories are in the form of a plurality of detachably secured dental floss members 300, toothpick means 400 in the form of tapered plastic coated end and included corner members of flap 201 and nail manicure means 500 comprising the flap closure receiving end adapted with different textures T1, T2, Tn of emery board material. Structure 200 is seen to comprise flap portion 201, on which an advertisement A may be placed, a back support portion 205, and a turned-up flap receiving end 203. The plurality of dental floss members 300 are secured to the flap receiving end portion 203 by staples 204. The dental floss members 300 are provided with perforation P on an enclosure 302 that provides means of separating individually packaged dental floss strands 301 having a length L of approximately 12 inches as well as containing a breath freshening substance 700, such as a mint flavored candy. The closure end of flap 201 are coated with a non-toxic plastic substance 401 that provides a rigid, moisture resistant, tapered end that results in toothpick useable corners 400. Coating 401 may be limited to corners 400 bounded by perforated line 402 which may be broken and disposed of after being used for toothpick purposes.

Figure 2:
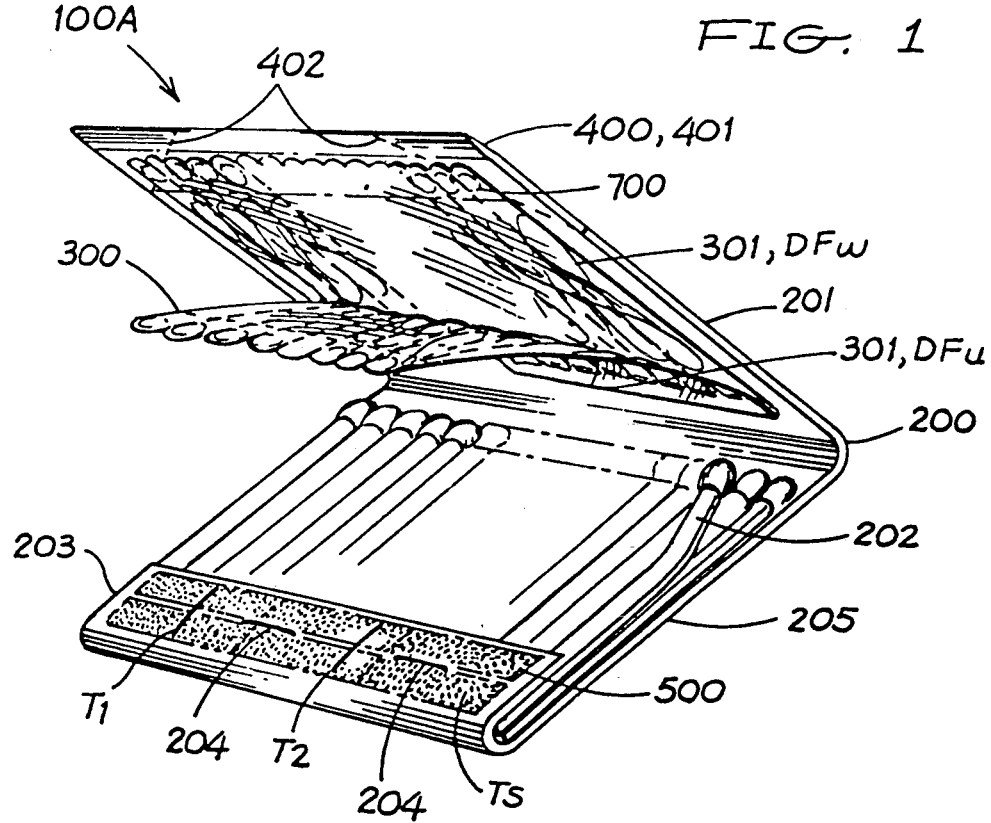
FIG. 2 is a perspective view of the present invention illustrating a matchbook-like structure with a plurality of detachable dental floss accessories and utilization of adapted portions of the matchbook-like structure for other personal care accessories and further including matches.

The utilization of the corners of flap portion 201 and the flap receiving end 203 as personal care accessories is an enhancement to existing matchbook structure manufacturing technology resulting in matchbook product 100A depicted in FIG. 2. Product 100A includes matches 202 and a dedicated match strike surface Ts along with the emery board strip 500 textures T1, T2. As another variation from product 100, the dental floss members 300 in product 100A are placed on the internal backside of flap 201 and include waxed dental floss strands DFw and unwaxed dental floss strands DFu.

Figure 3:
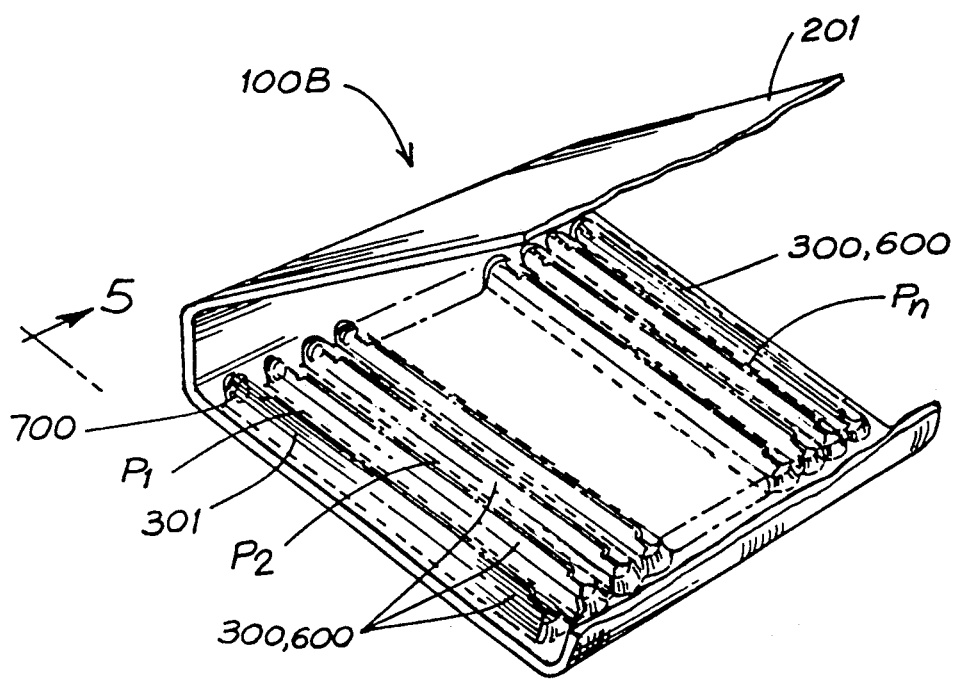
FIG. 3 is a perspective cutway view of the present invention wherein the plurality of detachable dental floss accessories are supported on rigid, individually perforated backing material.
Figure 4:
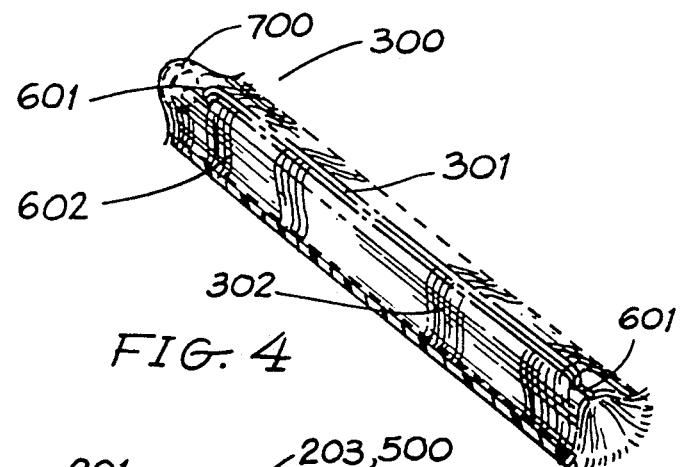
FIG. 4 is a perspecitve view of an individual dental floss member after being separated from the packaged accessories shown in FIG. 3.
Figure 5:
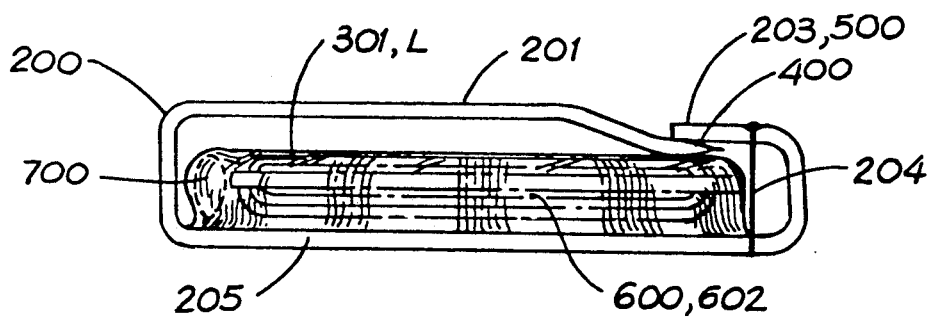
FIG. 5 is an cross-sectional end view taken along line 4—5 in FIG. 3 illustrating the enclosed length of dental floss looped about the rigid backing material and further showing the breath freshening substance packaged at one end.

FIG. 3 shows the present invention in the form of apparatus 100B where, instead of providing the dental floss strands 301 in loose individually wrapped strands, the plurality of dental floss members 300 are provided on a rigid backing member 600 that is secured to the flap receiving end 203 and back portion 205 of matchbook-like structure 200 utilizing staple 204, see FIG. 5. As best seen from FIGS. 4 and 5, the individual strands 301 are looped about an individual backing support portion 602 via grooves 601. Backing support structure 600 is provided with a plurality of perforations P1, P2, through Pn for convenient separation. Wrapping 302 is also perforated at P1, P2, and Pn to maintain the individually wrapped dental floss item depicted in FIG. 4. As an added feature, the apparatus 100B also includes a breath freshening substance 700 packaged with each dental floss member. The flap closure member 201 is also provided with toothpick usable corners 400 and closure flap receiving end 203 is also provided with emery board surface 500 for manicuring a user's nails.

FIG. 6 shows another embodiment 100C of the present invention where the plurality of dental floss members 300 consists of a plurality of rows of individual packages of strands 301 that have gripping ends 303 terminating at each end of strand 301 that are joined to adjacent gripping ends 303 via perforation P1, Px. One end of the plurality of gripping end members is secured between flap receiving end member 203 and back portion 205 using a staple 204 much like the other embodiments 100, 100A, and 100B that secure the plurality of dental floss members 300 to the matchbook-like structure. The apparatus 100C, additionally varies from the other embodiments by the manner of forming the closure end of flap portion 201 that provides the toothpick usable portion of the apparatus. Here, the end of flap 201 is provided with a plurality of elongated strips TP consisting of individual toothpick useable strips TP1, TP2 through TPn which have the tapered ends coated with a non-toxic plastic coating S and joined at perforation generally shown as Pa. Further, the emery board portion 500 is provided in the form of leafed tear-away emery board strips 501, 501n each having a predetermined texture Tn, varying from fine, medium and coarse. As in the other embodiments, flap portion can be used for placing a manufacturer's name and a breath freshening mint can be packaged with each individual dental floss member. FIG. 7 shows a cross sectional view of the embodiment 100C and depicts the feature of waxed and unwaxed dental floss strands, while FIG. 8 shows an individual dental floss member after being separated from the plurality of dental floss members and further illustrating the breath freshening mint contained within enclosure 302.

Therefore, while the present invention has been shown and described herein in what is believed to be the most practical and preferred embodiments, it is recognized that departures can be made therefore within the scope of the invention, which is therefore not to be limited to the details disclosed therein but is to be accorded the full scope of the claims so as to embrace any and all equivalent apparatus.

I claim:

1. A personal hygiene apparatus in matchbook form, said apparatus comprising:
   a folded matchbook-like structure;
   a plurality of a first personal hygiene accessory detachably secured to said structure, said plurality of a first personal hygiene accessory comprises individually packaged dental floss members including strands of dental floss having a predetermined length and an enclosure, each dental floss member being joined to an adjacent, similarly packaged dental floss member via perforated means between respective enclosures for easy tearing by a user, each one of said plurality of individually packaged dental floss members further comprising a breath freshing substance attached to an end of said individually packaged dental floss members; and
   at least one of a second personal hygiene accessory integral with said structure.

2. A personal hygiene apparatus as recited in claim 1, wherein: said breath freshening substance comprises a mint flavored candy.

3. A personal hygiene apparatus in matchbook form including a folded matchbook-like structure, said apparatus comprising:
   a plurality of individually packaged dental floss members detachably secured to said structure, each one of said plurality of individually packaged dental floss members comprising a strand of dental floss having a predetermined length and an enclosure, each dental floss member being joined to an adjacent, similarly packaged dental floss member via perforated means between respective enclosures for easy tearing by a user, each one of said plurality of individually packaged dental floss members further comprising a breath freshening substance attached to an end of said individually packaged dental floss members;
   pointed means integral with said structure for removing food particles from a user's teeth; and
   at least one abrasive material means detachably secured to said structure for manicuring a user's nails.

4. A method of producing a personal hygiene apparatus, said method comprising the steps of:
   providing a folded matchbook-like structure;
   attaching a plurality of individually packaged dental floss members to said structure;
   attaching a breath freshening substance at one end of each of said plurality of individually packaged dental floss members; and
   forming corner members of a closure flap portion of said structure with moisture resistant substance for producing a pointed means for removing food particles from a user's teeth.

* * * * *